(12) United States Patent
Burz et al.

(10) Patent No.: US 9,272,112 B2
(45) Date of Patent: *Mar. 1, 2016

(54) FOREHEAD PAD FOR A BREATHING MASK AND METHOD FOR MAKING THE SAME

(71) Applicant: ResMed R&D Germany GmbH, Martinsried (DE)

(72) Inventors: Johann S. Burz, Germaringen (DE); Achim Biener, Aufkirchen (DE); Bernd Lang, Graefelfing (DE)

(73) Assignee: ResMed R&D Germany GmbH, Martinsried (DE)

( * ) Notice: Subject to any disclaimer, the term of this patent is extended or adjusted under 35 U.S.C. 154(b) by 276 days.

This patent is subject to a terminal disclaimer.

(21) Appl. No.: 13/767,508

(22) Filed: Feb. 14, 2013

(65) Prior Publication Data

US 2013/0152939 A1 Jun. 20, 2013

Related U.S. Application Data

(63) Continuation of application No. 11/988,501, filed as application No. PCT/EP2006/007118 on Jul. 19, 2006, now Pat. No. 8,393,325.

(30) Foreign Application Priority Data

Jul. 19, 2005 (DE) .......... 10 2005 034 143

(51) Int. Cl.
*A61M 16/06* (2006.01)
(52) U.S. Cl.
CPC ........... *A61M 16/0683* (2013.01); *A61M 16/06* (2013.01); *A61M 16/0633* (2014.02)

(58) Field of Classification Search
CPC ............ A61M 16/06; A61M 16/0633; A61M 16/0605; A61M 2016/0661; A62B 18/00; A62B 18/02; A62B 18/08; A61B 5/6803; A41D 13/11; A41D 13/1146; A41D 13/1176; B29C 45/1657; B29C 45/1676; B29C 66/54
USPC ............ 128/203.29, 205.25, 206.21, 206.23, 128/206.24, 206.26, 206.28, 207.13
See application file for complete search history.

(56) References Cited

U.S. PATENT DOCUMENTS 2,749,910 A 6/1956 Faulconer
4,174,245 A * 11/1979 Martineau ............. B29C 45/006
156/245

(Continued)

FOREIGN PATENT DOCUMENTS

EP 1 099 452 A2 5/2001
GB 790677 2/1958

(Continued)

OTHER PUBLICATIONS

International Search Report for PCT/EP2006/007118 mailed Nov. 7, 2006.

(Continued)

*Primary Examiner* — Lynne Anderson
*Assistant Examiner* — Kathryn E Ditmer
(74) *Attorney, Agent, or Firm* — Nixon & Vanderhye P.C.

(57) ABSTRACT

A forehead pad for a breathing mask includes a substantially dimensionally stable first wall element and an elastomer second wall element coupled to the first wall element. The second wall element has a contact zone adapted to contact a surface of a user in use. The first and second wall elements define a filling-material-receiving chamber adapted to receive a filling material.

30 Claims, 5 Drawing Sheets

(56) References Cited

U.S. PATENT DOCUMENTS

| | | | |
|---|---|---|---|
| 4,175,562 A * | 11/1979 | Honan | 606/202 |
| 4,611,851 A * | 9/1986 | Noyes et al. | 297/199 |
| 4,803,029 A * | 2/1989 | Iversen et al. | 264/264 |
| 5,121,745 A * | 6/1992 | Israel | 128/202.28 |
| 5,800,402 A | 9/1998 | Bierman | |
| 6,409,954 B1 * | 6/2002 | Mulligan | B29C 41/04 264/255 |
| 6,467,483 B1 | 10/2002 | Kopacko et al. | |
| 8,393,325 B2 * | 3/2013 | Burz et al. | 128/206.24 |
| 2001/0039442 A1 * | 11/2001 | Gorge et al. | 607/109 |
| 2004/0149287 A1 | 8/2004 | Namey | |
| 2005/0199239 A1 | 9/2005 | Lang et al. | |
| 2005/0275141 A1 * | 12/2005 | Lange | 264/478 |
| 2007/0107733 A1 * | 5/2007 | Ho | A61M 16/06 128/206.24 |
| 2007/0215161 A1 * | 9/2007 | Frater et al. | 128/206.24 |
| 2009/0044806 A1 | 2/2009 | Burz et al. | |

FOREIGN PATENT DOCUMENTS

| | | |
|---|---|---|
| WO | WO 99/58198 | 11/1999 |
| WO | WO 03/035156 A2 | 3/2003 |
| WO | WO 03/105921 A2 | 12/2003 |

OTHER PUBLICATIONS

Written Opinion of the International Searching Authority for PCT/EP2006/007118.

* cited by examiner

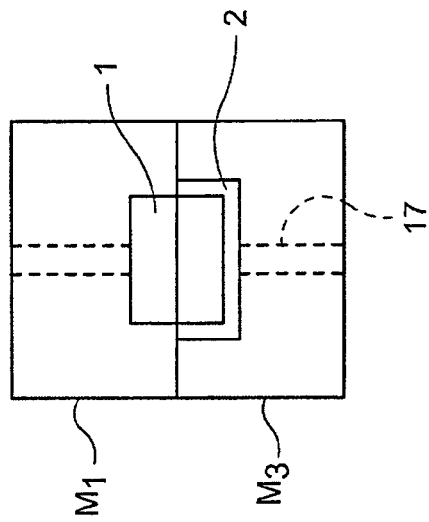
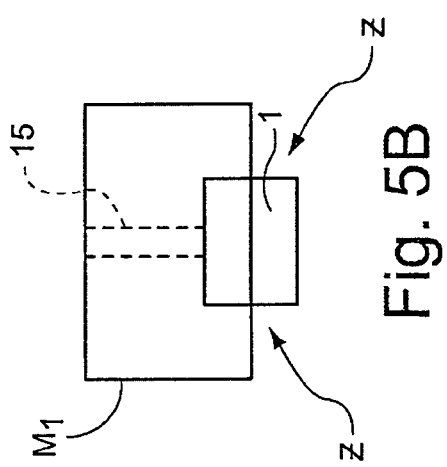
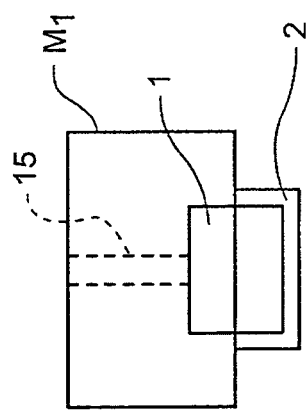
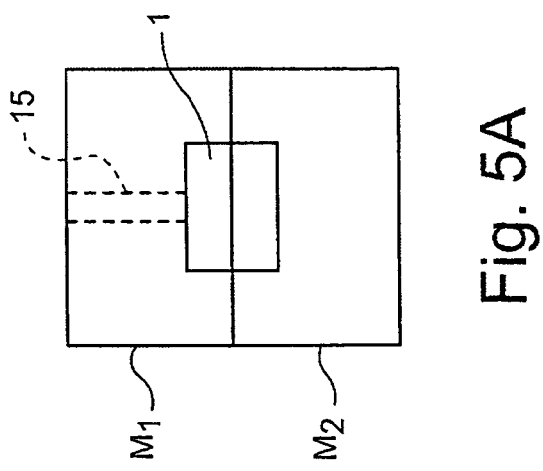

FOREHEAD PAD FOR A BREATHING MASK AND METHOD FOR MAKING THE SAME

CROSS-REFERENCE TO RELATED APPLICATION

This application is a continuation of U.S. patent application Ser. No. 11/988,501, filed Jan. 9, 2008, allowed, which is the U.S. National Phase of International Patent Application No. PCT/EP2006/007118, filed Jul. 19, 2006, which designated the U.S. and claims the priority of German Patent Application No. 10 2005 034 143.8, filed Jul. 19, 2005, the entire contents of each of which are hereby incorporated herein by reference.

FIELD OF THE INVENTION

The present invention relates to a structure for placement on a patient's face, and in particular to a forehead pad for a breathing mask.

BACKGROUND OF THE INVENTION

Breathing masks are used particularly for administering a breathable gas mixture, such as ambient air, at a pressure level that is above the ambient pressure. Delivering the breathing gas at a pressure level that is above the ambient pressure can serve for instance to perform CPAP therapy for treating stroke-related breathing problems or Obstructive Sleep Apnea (OSA).

A breathing mask for administering a breathable gas to a user is known from the International Patent Application PCT/EP02/11798 of the present Applicant, which is incorporated herein by reference in its entirety. By means of this breathing mask, it becomes possible, in collaboration with the surface of the face of a mask user, to seal off an interior of the breathing mask from the environment. Such breathing masks are used particularly in conjunction with medical or therapeutic administration of breathable gases as well as in the industrial field, such as in the field of respiratory protection. Typically, in these breathing masks, the sealing off of the surface of the face of the breathing mask user is achieved by means of a sealing lip structure extending all the way around the mask opening and pointing inward and seated on the surface of the face and made from an elastically deformable material. To keep the breathing mask in the application position, a headband device or headgear is typically used, which is wrapped around the region of the back of the user's head and forces the breathing mask against the surface of the user's face. The breathing mask may include a forehead pad, which makes bracing of the breathing mask possible in a region located above the bridge of the user's nose. The sealing action attained with such breathing masks having such sealing lips generally increases with the contact pressure against the surface of the face. When the contact pressures are high, long-term use of such breathing masks can be unpleasant and can cause pressure points in the region of the contact zones.

SUMMARY OF THE INVENTION

One aspect of the invention is to provide solutions to the above-described problem that make it possible to create a forehead pad which is distinguished by especially great wearing comfort and which in terms of manufacturing can be produced efficiently and inexpensively.

According to an aspect of the invention, a forehead pad for a breathing mask includes a substantially dimensionally stable first wall element and an elastomer second wall element coupled to the first wall element. The second wall element has a contact zone adapted to contact a surface of a user in use. The first and second wall elements define a filling-material-receiving chamber adapted to receive a filling material.

This arrangement creates a forehead pad for a breathing mask that may transmit the forces, possibly acting on the forehead support, with an advantageous distribution of pressure per unit of surface area.

In an embodiment of the invention, the filling-material-receiving chamber is formed by detachment of the second wall element from the first wall element. The filling-material-receiving chamber may be filled with a viscous medium, e.g., a gel material such as silicone gel. In an embodiment of the invention, the first wall element and the second wall element are coupled to one another in portions via one or more adhesion-bonding zones. The one or more adhesion-bonding zones may be generated by selective treatment of defined regions of the first wall element, e.g., by means of a corona or plasma treatment. It is also possible to generate the adhesion-bonding zone by other kinds of treatment of the first wall element, e.g., by applying adhesion promoters.

The forehead pad may be designed such that when viewed in a direction essentially perpendicular to the main surface it rests on, it has a substantially circular cross section or outline.

The forehead pad may have a polygonal or kidney-shaped outline and may be integrated with a suitable forehead support such that in the application position, the forehead pad is supported in a region of the forehead located over the eyebrows of the user.

The first wall element may be made from a thermoplastic material. The material properties of this plastic material may be selected such that the detachment of the elastomer material of the second wall element may be achieved without the addition of parting agents. Moreover, the plastic material intended for forming the first wall element may be selected such that the adhesion zone may be achieved reliably by suitable treatment, e.g., corona or plasma treatment.

The first wall element may also form an integral component of a structural part of a forehead support of the breathing mask. In particular, the first wall may form part of a forehead-support plate of a forehead support. The first wall element may also be embodied such that it may be coupled, including the same forehead support, to the forehead support in an easily replaced way. To that end, the first wall element may be provided with a fastener, such as a threaded or bayonet mounting structure.

Using the elastomer material, it is also possible to make other functional portions of the forehead pad, e.g., a pivot peg by way of which the forehead pad may be secured to the breathing mask.

Another aspect of the invention relates to a breathing mask for administering a breathable gas, at a pressure level that at least in one phase is above ambient pressure. The breathing mask includes a structure including a contact face adapted to contact a face surface portion on a user's face. The structure is formed by an elastomer wall and a counterpart surface structure. The elastomer wall and the counterpart surface structure define a filling-material-receiving chamber that extends therebetween. The elastomer wall is initially constructed as a wall that is formed integrally onto the counterpart surface structure and subsequently lifted from the counterpart surface structure.

Another aspect of the invention relates to a method for forming a forehead pad. The method includes providing a substantially dimensionally stable first wall element, molding an elastomer second wall element onto the substantially dimensionally stable first wall element, and introducing a filling material into a chamber defined between the first and second wall elements such that the second wall element detaches from the first wall element in regions that require detachment but remains attached to the first wall element in a defined adhesion bonding zone.

Another aspect of the invention relates to a method for forming a forehead pad. The method includes forming a first mold chamber with first and second tool segments to mold a substantially dimensionally stable first wall element; after the first wall element has hardened, removing the second tool segment from the first tool segment to expose a portion of the first wall element; treating the exposed portion of the first wall element to create an adhesion-bonding zone; forming a second mold chamber with the first tool segment and a third tool segment to mold an elastomer second wall element onto the substantially dimensionally stable first wall element; after the second wall element has hardened, removing the third tool segment from the first tool segment to expose the second wall element; and introducing a filling material into a chamber defined between the first and second wall elements such that the second wall element detaches from the first wall element in regions that require detachment but remains attached to the first wall element in the adhesion bonding zone.

Another aspect of the invention relates to a multi-part molding tool for forming a forehead pad including a first wall element and a second wall element. The multi-part molding tool includes a first tool segment, a second tool segment adapted to be positioned with respect to the first tool segment to form a first mold chamber to mold the first wall element, and a third tool segment adapted to be positioned with respect to the first tool segment after the second wall element is removed following molding of the first wall element. The third tool segment and the first tool segment adapted to form a second mold chamber to mold the second wall element onto the first wall element.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings:

FIG. 1b is a simplified sectional view illustrating the structure of a partially filled forehead pad, formed from the structure of FIG. 1a;

FIG. 1c is a simplified sectional view illustrating the structure of a filled forehead pad, formed from the structure of FIG. 1a;

FIGS. 5A-5D illustrate a production method for forming a forehead pad according to an embodiment of the invention.

DETAILED DESCRIPTION OF ILLUSTRATED EMBODIMENTS

Figure 1A:
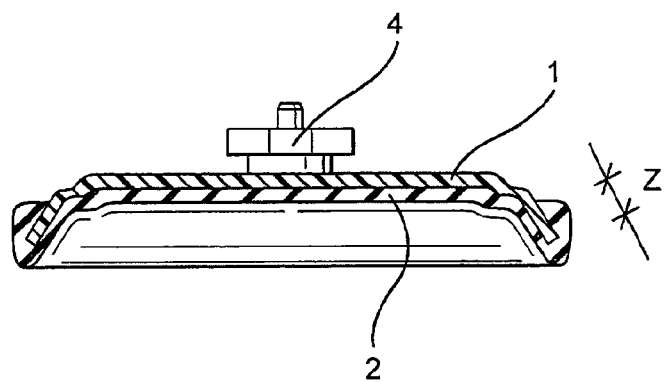
FIG. 1a is a simplified sectional view illustrating the structure of a forehead pad according to an embodiment of the invention, in an unfilled state.

In FIG. 1a, a preliminary stage of a forehead pad according to an embodiment of the invention for a breathing mask is shown. The forehead pad includes a substantially dimensionally stable first wall element 1, e.g., made from a thermoplastic material or a metal material, and an elastomer second wall element 2, coupled to the first wall element 1. The second wall element 2, in the state shown in FIG. 1c, forms a contact zone 3 intended for contacting the surface S of a user's forehead. The forehead pad shown in FIGS. 1a to 1c also includes securing structures 4, by way of which the forehead pad can be attached to a forehead support of a breathing mask. It is also possible to embody the first wall element 1 as a component of the forehead support, e.g., integrally form the first wall element 1 with the forehead support.

The second wall element 2 shown in FIG. 1a is formed by injection molding an elastomer material, e.g., liquid silicone rubber (LSR), onto the first wall element 1. The filling-material-receiving chamber GA that can be seen in FIGS. 1b and 1c, which is intended for receiving a filling material, is formed by detachment of the second wall element 2 from the first wall element 1. Detachment is made possible by selecting the surface properties of the first wall element 1 such that in the surface region that requires detachment, no adhesive bond is created between the elastomer material of the second wall element 2 and the first wall element 1. In the illustrated embodiment, an outer circumferential region of the first wall element 1 is treated such that a defined adhesion-bonding zone Z is created here. The adhesion-bonding zone can be generated by corona or plasma treatment. It is also possible to generate this adhesion-bonding zone by applying an adhesion promoter.

The filling-material-receiving chamber GA may be filled with a viscous medium, e.g., a jelly-like or gel-like medium, such as partly cross-linked silicone rubber. It is also possible to fill the filling-material-receiving chamber GA with a gaseous medium or a relatively low-viscosity medium, such as water.

Figure 1B:
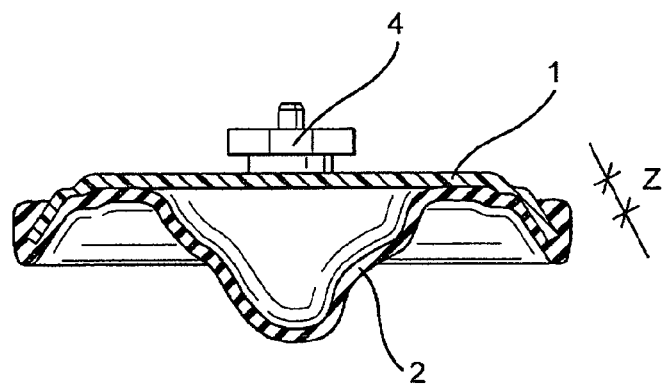
Figure 1C:
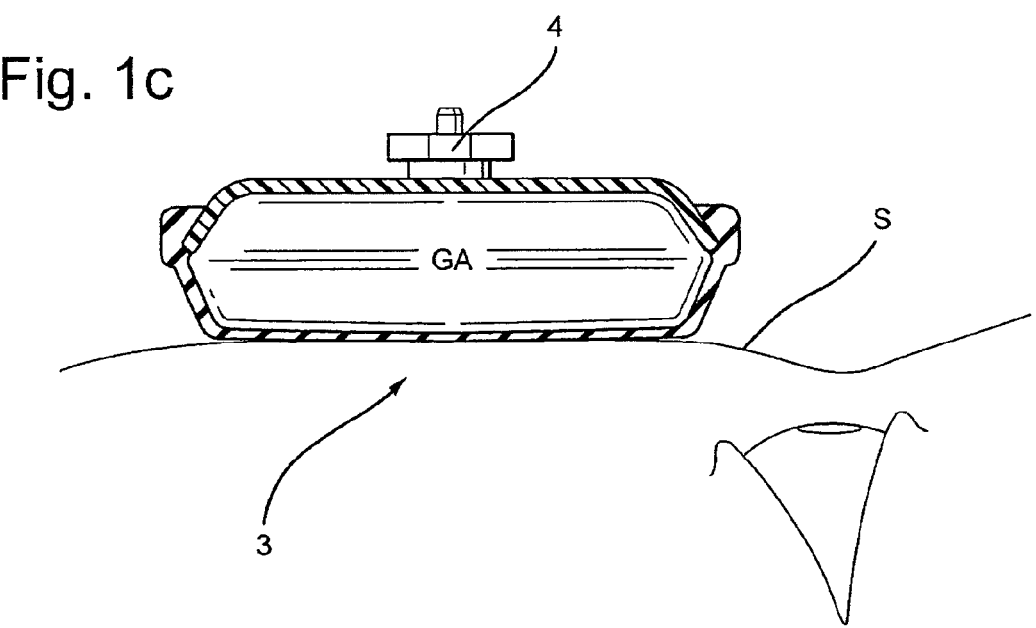

FIG. 1a illustrates the forehead pad in its unfilled state wherein the elastomer second wall element 2 is molded onto the first wall element 1. As the filling material is introduced into the chamber GA, the second wall element 2 detaches from the first wall element 1 in the regions that require detachment but remains attached to the first wall element 1 in the defined adhesion bonding zone Z, i.e., the outer circumferential or perimeter region of the first wall element 1. FIG. 1b illustrates the forehead pad in a partially filled state wherein the second wall element 2 begins to detach from the first wall element 1. FIG. 1c illustrates the forehead pad in a filled state wherein the chamber GA is completely filled with the filling material.

Figure 2:
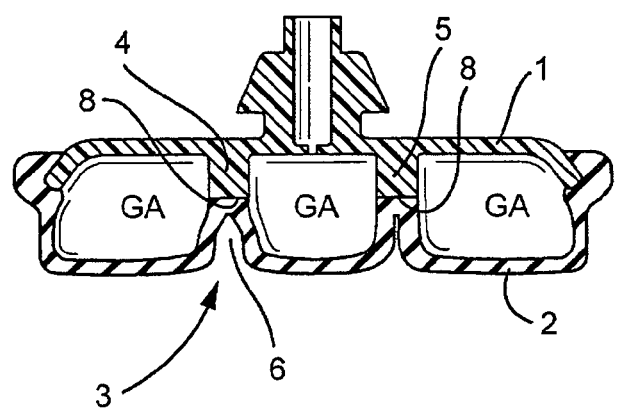
FIG. 2 is a sectional view illustrating the structure of a forehead pad according to another embodiment of the invention whose contact zone is made up of a plurality of beads.

In FIG. 2, a further variant of a forehead pad according to another embodiment of the invention is shown. In this variant, the first wall element 1 is provided with ribs 4, 5, by which the gel-receiving chamber GA is partitioned off. Moreover, the ribs 4, 5 generate additional adhesion-bonding points 8, which prevent disproportionate lifting off of the second wall element 2 from the first wall element 1. The ribs 4, 5 may be dimensioned such that in the region of the face-contact zone 3 they create small channels 6, which enables ventilation of the surface of the contact zone 3 that rests on the surface of the user's forehead.

In an embodiment, the chamber GA may include two or more partitions that are communicated with one another such that the partitions can be filled with a filling material via one inlet port. In another embodiment, the chamber GA may include two or more partitions that are isolated from one another such that the partitions are filled with a filling material via two or more inlet ports, e.g., inlet port for each partition. In such an arrangement, the isolated partitions may be filled with different filling materials to provide different rigidities in different regions of the forehead pad.

Figure 3:
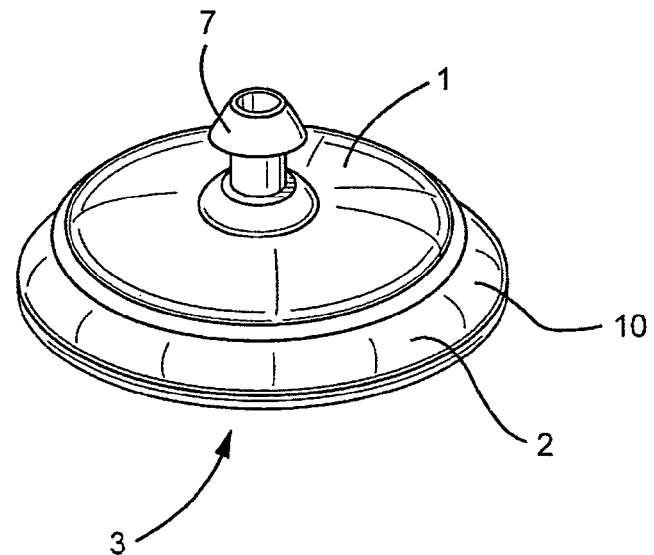
FIG. 3 is a perspective view illustrating the structure of a forehead pad according to another embodiment of the invention, having a substantially circular outline.

In FIG. 3, a variant of a forehead pad according to another embodiment of the invention with a substantially circular outline is shown. The forehead pad may be filled with a filling material, e.g., a gel, in such a way that an outer circumferential or perimeter region of the second wall element 2 includes a bead portion 10 that extends in beadlike fashion around the circumferential edge of the first wall element 1. On a side of the forehead pad facing away from the face-contact zone 3, a securing peg 7 is provided, by way of which the forehead pad can be fixed to a suitable structure of a breathing mask. It is possible to form peg 7 with a filling conduit through which gel is provided to the filling-material-receiving chamber GA (e.g., see FIG. 1c).

Figure 4:
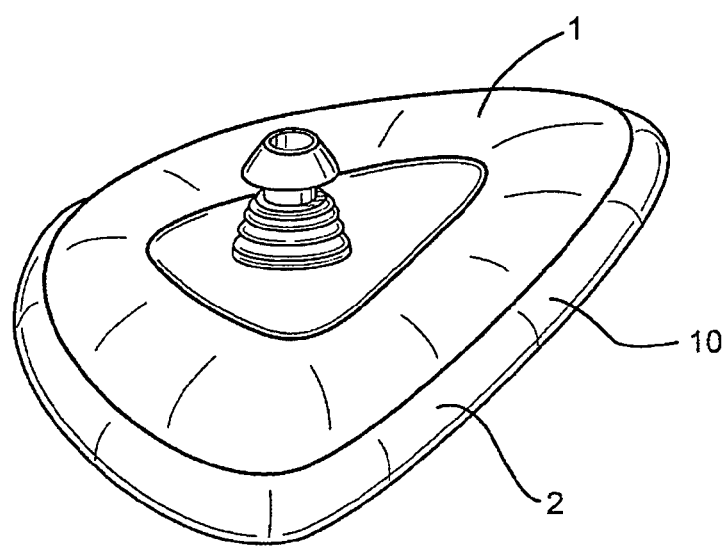
FIG. 4 is a perspective view illustrating the structure of a forehead pad according to another embodiment of the invention, having a substantially kidney-shaped outline.

In FIG. 4, a variant of the forehead pad according to another embodiment of the invention is shown which has a substantially kidney-shaped outline. To achieve this kidney-shaped outline, the first wall element 1 and the second wall element 2, initially injection molded onto it, are shaped accordingly. By filling the filling-material-receiving chamber formed between the two wall elements 1, 2, it becomes possible to inflate the second wall element 2 in such a way that it forms a relatively soft bead portion 10 that projects radially past the first wall element 1 (e.g., in a manner similar to that of FIG. 3).

By special adaptation of the local wall thicknesses of the second wall element, it is possible to vary the force transmission behavior, e.g., the reduction in pressure per unit of surface area, toward the edge of the face-contact zone.

The invention is not limited to the exemplary embodiments described above. In particular, the invention is not limited to forehead pads for breathing masks. For example, aspects of the invention may be suitable for making structure for placement on the faces of the kind employed with eyeglasses.

The production of the forehead pad according to embodiments of the invention, or a corresponding structure for placement on the face, may be done largely in fully automated fashion by multi-part tools. For example, as shown in FIG. 5A, it is possible to use a multi-part molding tool including tool segments $M_1$ and $M_2$ for producing the first wall element 1, which first forms only the mold chamber required for forming the first wall element 1. The plastic material may enter the mold chamber defined by tool segments $M_1$ and $M_2$ via channel 15. After the plastic material placed in this mold chamber has hardened, the molding tool may be opened by removing tool segment $M_2$, as shown in FIG. 5B. As illustrated, the first wall element 1 may be treated to create an adhesion-bonding zone Z as described above. The treating may occur at any one of the steps shown in FIGS. 5A to 5C, and may be incorporated into one of the tool segments $M_2$ or $M_3$. Next, as shown in FIG. 5C, the molding tool is closed by means of a new tool segment $M_3$, which itself, in cooperation with the remaining tool segment $M_1$ and with the first wall element 1, defines a mold chamber of the kind needed for forming the second wall element 2. This mold chamber may now be filled with an elastomer plastic material, e.g., LSR, via channel 17. After the second plastic material has hardened, the tool segment $M_3$ may be removed and a viscous medium, e.g., silicone gel, may be introduced via channel 15 in $M_1$ into a conduit embodied in the first wall element 1, and into a boundary region defined between the second wall element 2 and the first wall element 1 as shown in FIG. 5D. By successive introduction of the appropriate filling material, the second wall element 2 is lifted from the first wall element 1, thus forming a gel cushion. The filling conduit for introducing the gel material may also be closed in automated fashion.

Figure 6:
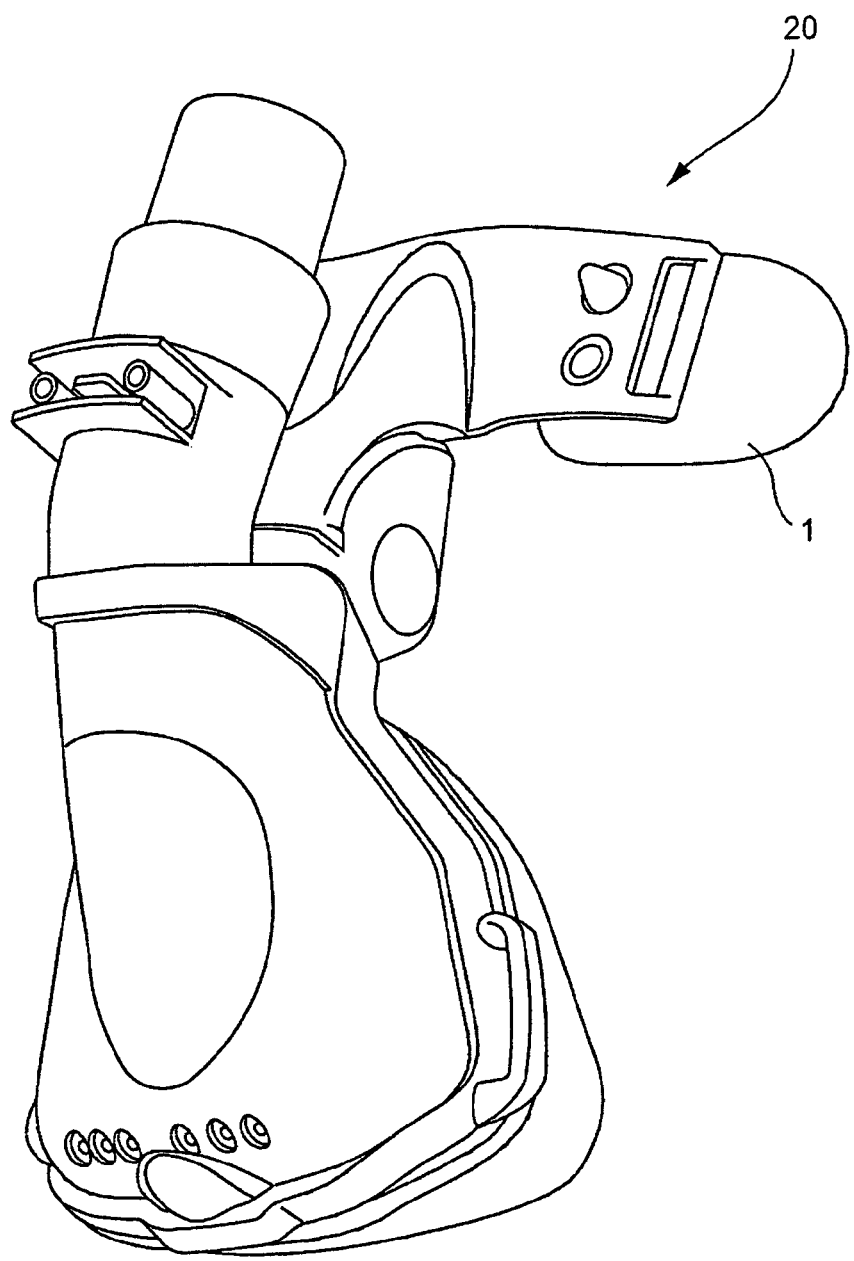
FIG. 6 is a perspective view of a breathing mask including a forehead pad according to an embodiment of the invention.

FIG. 6 illustrates a breathing mask 20 including a forehead pad with first and second wall elements 1, 2 such as those described above. Further details of the breathing mask are described in PCT/EP02/11798, which is incorporated herein by reference in its entirety.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A forehead pad for a breathing mask, comprising:
a substantially dimensionally stable first wall element; and
an elastomer second wall element comprising a contact zone adapted to contact a surface of a user when the breathing mask is worn,
wherein the first and second wall elements define a filling-material-receiving chamber adapted to receive a filling material,
wherein the first wall element has an attachment zone and a detachment zone, the second wall element being temporarily attached to the first wall element in the detachment zone prior to the filling-material-receiving chamber receiving the filling material, and
wherein the second wall element is configured to detach from the detachment zone of the first wall element when the filling-material is received in the filling-material-receiving chamber.

2. The forehead pad in accordance with claim 1, wherein the elastomer second wall element is molded onto the first wall element.

3. The forehead pad in accordance with claim 1, wherein the attachment zone is an adhesion-bonding zone.

4. The forehead pad in accordance with claim 3, wherein the adhesion-bonding zone has a first surface property which allows the second wall element to bond to the first wall element, and the detachment zone has a second surface property which disallows bonding between the second wall element and the first wall element.

5. The forehead pad in accordance with claim 1, wherein the pad further comprises ribs for partitioning the filling-material-receiving chamber.

6. The forehead pad in accordance with claim 5, wherein the ribs are dimensioned so as to create ventilation channels in the contact zone.

7. The forehead pad in accordance with claim 5, wherein at least two partitions are filled with different materials to provide different rigidities in different regions of the forehead pad.

8. The forehead pad in accordance with claim 1, wherein the second wall element is formed by injection molding an elastomer material onto the first wall element.

9. The forehead pad in accordance with claim 1, wherein the filling-material-receiving chamber is formed by detachment of the second wall element from the first wall element.

10. The forehead pad in accordance with claim 1, wherein the filling-material-receiving chamber is filled with a gel material.

11. The forehead pad in accordance with claim 1, wherein the filling-material-receiving chamber is filled with a gaseous medium.

12. The forehead pad in accordance with claim 3, wherein the first wall element and the second wall element are coupled to one another via the adhesion-bonding zone.

13. The forehead pad in accordance with claim 4, wherein the adhesion-bonding zone is formed by corona or plasma treatment of defined and selected regions of the first wall element.

14. The forehead pad in accordance with claim 1, wherein the forehead pad has a substantially circular outline.

15. The forehead pad in accordance with claim 1, wherein the e forehead pad has a polygonal or kidney-shaped outline.

16. The forehead pad in accordance with claim 1, wherein the first wall element is made from a thermoplastic material.

17. The forehead pad in accordance with claim 1, wherein the first wall element is part of a forehead support.

18. The forehead pad in accordance with claim 1, wherein the first wall element is provided with a fastener to couple the first wall element to a forehead support.

19. A breathing mask including a forehead pad in accordance with claim 1.

20. A forehead pad for a breathing mask, comprising:
a substantially dimensionally stable first will element; and
an elastomer second wall element comprising a contact zone adapted to contact a surface of a user when the breathing mask is worn,
wherein the first and second wall elements define a filling-material-receiving chamber adapted to receive a filling material,
wherein the first wall element has an attachment zone and a detachment zone, the second wall element being attached to the first wall element in the attachment zone and the detachment zone prior to the filling-material-receiving chamber receiving the filling material, and
wherein the attachment of the second wall element to the first wall element in the attachment zone has a greater strength than the attachment of the second wall element to the first wall element in the detachment zone such that the second wall element is configured to detach from the first wall element in the detachment zone when the filling-material is received in the filling-material-receiving chamber.

21. The forehead pad in accordance with claim 20, wherein the attachment of the second wall element to the first wall element in the attachment zone is a permanent attachment that extends along an outer circumferential region of the first wall element.

22. The forehead pad in accordance with claim 21, wherein the attachment of the second wall element to the first wall element in the detachment zone is a temporary attachment disposed inside the outer circumferential region.

23. The forehead pad in accordance with claim 20, wherein the attachment zone is an adhesion-bonding zone.

24. The forehead pad in accordance with claim 23, wherein the adhesion-bonding zone has a first surface property which allows the second wall element to bond to the first wall element, and the detachment zone has a second surface property which disallows bonding between the second wall element and the first wall element.

25. The forehead pad in accordance with claim 23, wherein the adhesion-bonding zone is formed by corona or plasma treatment of defined and selected regions of the first wall element.

26. The forehead pad in accordance with claim 20, wherein the second wall element is formed by injection molding an elastomer material onto the first wall element.

27. The forehead pad in accordance with claim 20, wherein the filling-material-receiving chamber is formed by detachment of the second wall element from the first wall element.

28. The forehead pad in accordance with claim 20, wherein the filling-material-receiving chamber is filled with a gel material.

29. The forehead pad in accordance with claim 20, wherein the filling-material-receiving chamber is filled with a gaseous medium.

30. A breathing mask including a forehead pad in accordance with claim 20.

* * * * *

UNITED STATES PATENT AND TRADEMARK OFFICE
CERTIFICATE OF CORRECTION

PATENT NO. : 9,272,112 B2
APPLICATION NO. : 13/767508
DATED : March 1, 2016
INVENTOR(S) : Burz et al.

Page 1 of 1

It is certified that error appears in the above-identified patent and that said Letters Patent is hereby corrected as shown below:

In the claims:

In claim 20 at column 7, line 38, "a substantially dimensionally stable first will element, and" should be corrected to ---a substantially dimensionally stable first wall element, and---

Signed and Sealed this
Fourteenth Day of June, 2016

Michelle K. Lee
*Director of the United States Patent and Trademark Office*